US008880144B2

(12) United States Patent
Kang et al.

(10) Patent No.: US 8,880,144 B2
(45) Date of Patent: Nov. 4, 2014

(54) PET DETECTOR MODULE USING GAPD COMPOSED OF LARGE AREA MICRO-CELLS

(75) Inventors: Jihoon Kang, Jeollanam-do (KR); Yong Choi, Seoul (KR); Key Jo Hong, Seoul (KR); Wei Hu, Seoul (KR); Yoon Suk Huh, Seoul (KR); Hyun Keong Lim, Seoul (KR); Sangsu Kim, Seoul (KR)

(73) Assignee: Industry—University Cooperation Foundation Sogang University, Seoul (KR)

( * ) Notice: Subject to any disclaimer, the term of this patent is extended or adjusted under 35 U.S.C. 154(b) by 960 days.

(21) Appl. No.: 12/904,584

(22) Filed: Oct. 14, 2010

(65) Prior Publication Data

US 2011/0263965 A1    Oct. 27, 2011

(30) Foreign Application Priority Data

Apr. 26, 2010    (KR) ........................ 10-2010-0038418

(51) Int. Cl.
| | | |
|---|---|---|
| *A61B 5/05* | (2006.01) | |
| *A61B 6/03* | (2006.01) | |
| *A61B 6/00* | (2006.01) | |
| *A61B 5/055* | (2006.01) | |
| *G01T 1/29* | (2006.01) | |
| *G01R 33/48* | (2006.01) | |

(52) U.S. Cl.
CPC .............. *G01T 1/2985* (2013.01); *A61B 6/037* (2013.01); *A61B 6/5235* (2013.01); *G01R 33/481* (2013.01); *A61B 6/4258* (2013.01); *A61B 5/055* (2013.01); *G01T 1/2935* (2013.01)
USPC .. 600/411; 600/436; 250/363.03; 250/363.04

(58) Field of Classification Search
None
See application file for complete search history.

(56) References Cited

U.S. PATENT DOCUMENTS

| | | | | |
|---|---|---|---|---|
| 2005/0006589 A1* | 1/2005 | Joung et al. | .............. | 250/370.09 |
| 2007/0102641 A1* | 5/2007 | Schmand et al. | ........ | 250/363.03 |
| 2008/0156993 A1* | 7/2008 | Weinberg et al. | ........ | 250/363.03 |
| 2009/0008566 A1* | 1/2009 | Agarwal et al. | .......... | 250/370.11 |
| 2009/0236532 A1* | 9/2009 | Frach et al. | .............. | 250/363.04 |
| 2010/0065746 A1* | 3/2010 | Grazioso et al. | ......... | 250/363.04 |

OTHER PUBLICATIONS

Cuddy, S. et al., *Effect of Scintillator Crystal Geometry and Surface Finishing on Depth of Interaction Resolution in PET Detectors—Monte Carlo Simulation and Experimental Results Using Silicon Photomultipliers*, Proc. of SPIE, vol. 7622 (2010), pp. 762210-1-762210-8.
Braem, A. et al., *AX-PET: A Novel PET Detector Concept with Full 3D Reconstruction*, Nuclear Instruments and Methods in Physics Research A 610 (2009) 192-195.

* cited by examiner

*Primary Examiner* — Unsu Jung
*Assistant Examiner* — Michael N Fisher
(74) *Attorney, Agent, or Firm* — Alston & Bird LLP

(57) ABSTRACT

Provided is a positron emission tomography (PET) detector module using Geiger-mode avalanche photodiode (GAPD) as a photosensor. The PET detector module includes: a PET detector unit with a scintillation crystal detecting gamma rays emitted from a living body and converting them into a scintillation light and a first GAPD photosensor and a second GAPD photosensor each being connected to either end of the scintillation crystal and converting the scintillation light into an electrical signal; and a depth of interaction (DOI) decoding unit receiving the signals from the PET detector unit and comparing amplitude of the signals detected by the first GAPD photosensor and the second GAPD photosensor, thereby providing the depth information where the gamma rays are incident on the scintillation crystal (DOI). The disclosed PET detector module can provide improved energy resolution and additional DOI information while maintaining linearity.

15 Claims, 14 Drawing Sheets

GAPD Photosensor with small-area microcells

GAPD Photosensor with large-area microcells

PET DETECTOR MODULE USING GAPD COMPOSED OF LARGE AREA MICRO-CELLS

CROSS-REFERENCE TO RELATED APPLICATIONS

This application claims priority under 35 U.S.C. §119 to Korean Patent Application No. 10-2010-0038418, filed on Apr. 26, 2010, in the Korean Intellectual Property Office, the disclosure of which is incorporated herein by reference in its entirety.

TECHNICAL FIELD

The following disclosure relates to a positron emission tomography (PET) detector using a PET detector module and a PET fusion medical imaging device using the same. More particularly, the following disclosure relates to a PET detector module using a Geiger-mode avalanche photodiode (GAPD) as a photosensor, a PET detector using the same and a PET fusion medical imaging device using the same.

BACKGROUND

Medical imaging employed for cellular, pre-clinical and clinical tests and diagnosis of patients is largely classified into structural imaging and functional imaging. Structural imaging refers to structural and anatomical of the human body, and functional imaging refers to imaging of functional information of the cognitive, sensual or other functions of the human body in a direct or indirect manner. The structural or anatomical imaging technique includes computed tomography (CT), magnetic resonance imaging (MRI), or the like. For imaging of functional information about the human body's physiological and biochemical functions, positron emission tomography (PET) is widely used.

PET is a powerful biological imaging tool allowing monitoring of the functional processes of the human body in a noninvasive manner. A biological probe molecule labeled with a radioactive, positron-emitting isotope is injected into the body, and the distribution of radiation is reconstructed through tomography to visualize and quantify the physiological and biochemical responses in the body organs. The functional and molecular biological information about the brain or other organs provided by PET may be useful for the etiological study of disease, diagnosis, prognosis, monitoring after anticancer treatment, or the like.

In order to provide functional information of the human body tissues with a high sensitivity of molecular level and to overcome the problem of low resolution, PET fusion medical imaging devices such as PET-CT, PET-MRI and PET-optical imaging are being developed.

FIG. 1a is a perspective view of a PET system and FIG. 1b is an enlarged perspective view of a PET detector in the PET system.

Referring to FIGS. 1a and 1b, a PET system 100 includes a PET detector 120, a cable 130 one end of which is connected to the PET detector 120, and a PET circuitry 140 connected to the other end of the cable 130. A bed 111 for transferring a patient is provided movably on a support 113, and the PET detector 120 is provided in an imaging bore (not shown) with a tubular form configured to allow a patient to be placed therein. On one end, a plurality of scintillation crystals 121 are arranged in annular shape to form a scintillation crystal array 122. The scintillation crystal array 122 is arranged in plural numbers along a length direction of the PET detector 120. The other end of the scintillation crystals 121 is connected to a photosensor, thereby configuring the PET detector 120. The photosensor (not shown) of the PET detector 120 converts the scintillation from the scintillation crystals 121 into an electrical signal. The photosensor may be a photomultiplier tube (PMT), a positive-intrinsic-negative PIN) diode, cadmium telluride (CdTe), cadmium zinc telluride (CZT), an avalanche photodiode (APD), a Geiger-mode avalanche photodiode (GAPD), or the like.

The PMT was developed in 1974 and is currently the most frequently used photosensor in a PET device. Quantum efficiency is usually 25-30%. Recently, it was improved to 40% or higher. It is characterized by a high signal amplification factor and low noise characteristics and is advantageous in that the operation is very stable. However, high bias voltage requirement and sensitivity to magnetic field make it difficult to be applied in fusion imaging devices such as PET-MR.

Of late, semiconductor photosensors that can be used in a magnetic field were developed. Especially, the GAPD is viewed as a promising next-generation photosensor that can replace the PMT, because of high signal amplification factor, low noise characteristics, mass producibility, magnetic resonance (MR) compatibility and operability at low bias voltage. In general, the GAPD is a 4-9 $mm^2$ sized photosensor composed of a plurality of micro-cells having a size of tens to hundreds of micrometers arranged in two dimensions. Each micro-cell consists of an APD operating in Geiger mode. When a photon is incident, an electron is emitted typically with an amplification factor of $10^6$ times. Then, it returns to the original state as the avalanche is quenched by a quenching resistance of 100 kΩ to 1 MΩ. That is to say, each micro-cell performs on/off switch operation that detects presence or absence of photon incidence. Assuming that one gamma ray reaches the scintillation crystal and then incident on the GAPD after being converted into multiple photons, the intensity of the incident gamma ray can be calculated by counting the number of the micro-cells with on reactions.

However, for the GAPD to be utilized as the PET detector, the linearity problem for the 511 keV gamma ray has to be solved. For this reason, the GAPD consisting of many micro-cells is commonly used in spite of low quantum efficiency. Although the GAPD having a smaller number of cells per unit area and thus having high quantum efficiency can provide improved energy resolution, it is inapplicable to the PET detector because of the linearity problem for the 511 keV gamma ray.

SUMMARY

The present disclosure is directed to providing a positron emission tomography (PET) detector module using a Geiger-mode avalanche photodiode (GAPD) photosensor, which is capable of providing improved energy resolution and additional depth of interaction (DOI) information while maintaining linearity, a PET detector using the same, and a PET fusion medical imaging device using the same.

In one general aspect, the present disclosure provides a PET detector module including: a PET detector unit including a scintillation crystal detecting gamma rays emitted from a living body and converting them into a scintillation light and a first GAPD photosensor and a second GAPD photosensor each being connected to either end of the scintillation crystal and converting the scintillation light into an electrical signal; and a DOI decoding unit receiving the signals from the PET detector unit and comparing amplitude of the signals detected by the first GAPD photosensor and the second GAPD photosensor, thereby providing the depth information where the gamma rays are incident on the scintillation crystal (hereinafter, referred to as DOI).

The first GAPD photosensor and the second GAPD photosensor may be a GAPD including micro-cells with a large area of 10 μm² or larger.

The PET detector module may further include a signal processing unit providing information about energy of the incident gamma rays and reaction time from a combination of a signal output from the DOI decoding unit and the signals from the PET detector unit.

The scintillation crystal may be selected from bismuth germanate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr$_3$), lutetium iodide (LuI$_3$), gadolinium oxyorthosilicate (GSO), lutetium gadolinium oxyorthosilicate (LGSO) and lutetium aluminum garnet (LuAG).

In another general aspect, the present disclosure provides a PET detector module including: a PET detector unit comprising a scintillation crystal detecting 511 keV gamma rays emitted from a living body through a pair annihilation phenomenon toward opposite directions and converting them into a scintillation light and a first GAPD photosensor and a second GAPD photosensor each being connected to either end of the scintillation crystal and converting the scintillation light into an electrical signal; a signal amplification unit receiving the signals detected by the first GAPD photosensor and the second GAPD photosensor and amplifying the signals; and a DOI decoding unit receiving the signals from the signal amplification unit and comparing amplitude of the signals detected by the first GAPD photosensor and the second GAPD photosensor, thereby determining the position where the gamma rays are incident on the scintillation crystal (DOI).

In another general aspect, the present disclosure provides a PET detector module including a PET detector unit including a scintillation crystal detecting 511 keV gamma rays emitted from a living body through a pair annihilation phenomenon toward opposite directions and converting them into a scintillation light and a first GAPD photosensor and a second GAPD photosensor each being connected to either end of the scintillation crystal and converting the scintillation light into an electrical signal, arranged in a matrix form, in a polygonal shape or in a ring shape so as to extend a detection area.

In another general aspect, the present disclosure provides a PET detector module including a PET detector unit including a scintillation crystal detecting 511 key gamma rays emitted from a living body through a pair annihilation phenomenon toward opposite directions and converting them into a scintillation light and a first GAPD photosensor and a second GAPD photosensor each being connected to either end of the scintillation crystal and converting the scintillation light into an electrical signal, connected and arranged in ring shape.

In another general aspect, the present disclosure provides a PET-magnetic resonance imaging (MRI) fusion system comprising: an MRI bore allowing a patient to be placed therein and scanning magnetic resonance (MR) images; a PET detector provided in the MRI bore and comprising a scintillation crystal detecting gamma rays emitted from a living body and converting them into a scintillation light and a first GAPD photosensor and a second GAPD photosensor each being connected to either end of the scintillation crystal and converting the scintillation light into an electrical signal, connected and arranged in cylindrical shape; and a circuitry processing signals about the MR images from the MRI bore and the signals from the PET detector and reconstruct the MR images and images from the PET signals.

The PET detector module according to the disclosure is capable of providing improved energy resolution and additional DOI information while maintaining linearity. The PET detector module exhibits significantly improved linearity and energy resolution. It is applicable to clinical and preclinical PET, especially as a PET detector for scanning small animals, breasts or brain.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

Figure 1A:
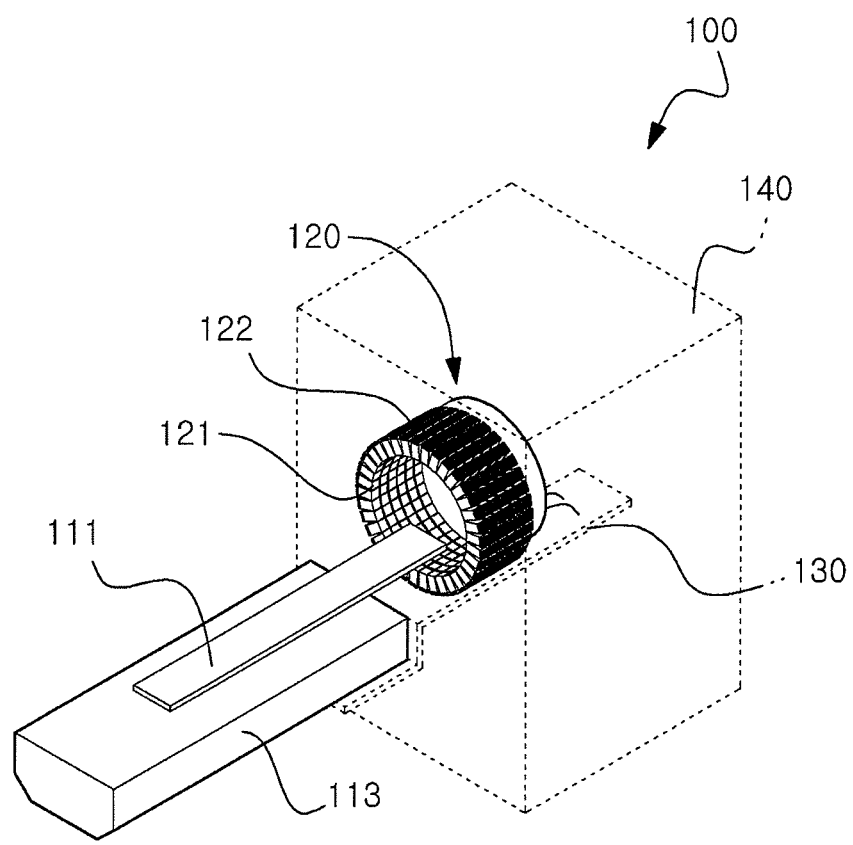
FIG. 1a is a perspective view of a positron emission tomography (PET) system and FIG. 1b is an enlarged perspective view of a PET detector in the PET system.
Figure 1B:
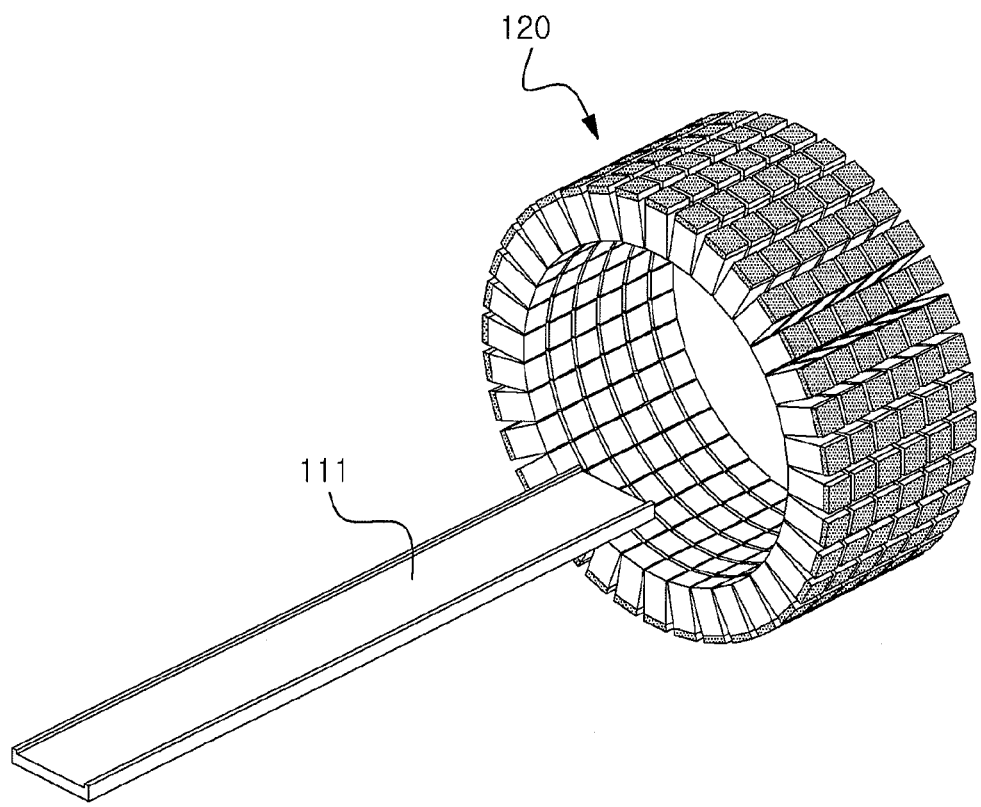

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

DETAILED DESCRIPTION OF EMBODIMENTS

Hereinafter, description will be made about particular embodiments of the present disclosure which may be variously modified. However, it is not intended to limit the present disclosure to specific embodiments. On the contrary, the present disclosure is intended to cover not only the exemplary equivalents but also various alternatives, modifications, equivalents and other equivalents that may be included within the spirit and scope the present disclosure are.

While terms including ordinal numbers, such as "first", "second", etc., may be used to describe various components, such components are not limited to the above terms. Those terms are used only to distinguish one component from another. For example, without departing from the scope of the present disclosure, a first component may be referred to as a second component, and likewise a second component may be referred to as a first component. The term and/or encompasses both combinations of the plurality of related items disclosed and any one item from among the plurality of related items disclosed.

When a component is mentioned to be "connected" to or "accessing" another component, this may mean that it is directly connected to or accessing the other component, but it is to be understood that another component may exist in between. On the other end, when a component is mentioned to be "directly connected" to or "directly accessing" another component, it is to be understood that there are no other components in between.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including", "having", etc. are intended to indicate the existence of the features, numbers, operations, components, parts or combinations thereof disclosed in the specification, and are not intended to preclude the possibility that one or more other features, numbers, operations, components, parts or combinations thereof may exist or may be added.

Unless otherwise defined, all terms used herein, including technical and scientific terms, have the same meanings as those generally understood by those with ordinary knowledge in the field of art to which the present disclosure belongs. Such terms as those defined in a generally used dictionary are to be interpreted to have the meanings equal to the contextual meanings in the relevant filed of art, and are not to be interpreted to have ideal or excessively formal meanings unless clearly defined in the present specification.

Certain embodiments of the present disclosure will be described below in more detail with reference to the accompanying drawings, in which those components are rendered the same reference numeral that are the same or are in correspondence, regardless of the figure number, and redundant explanations are omitted.

Figure 2:
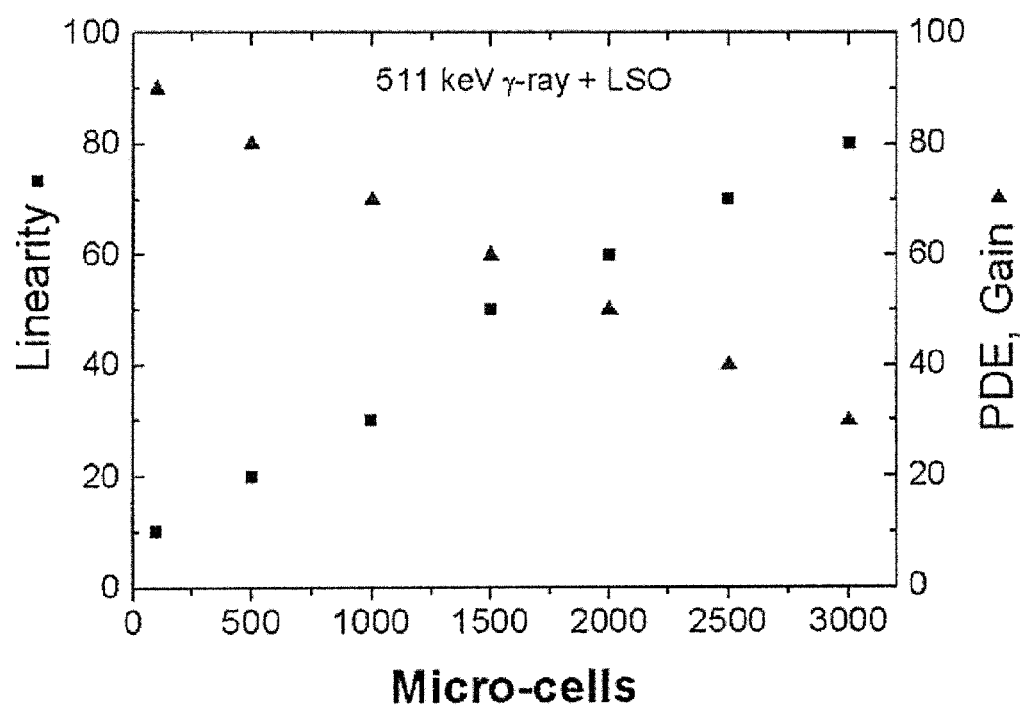
FIG. 2 is a graph showing a relationship between the number of micro-cells of a Geiger-mode avalanche photodiode (GAPD) of a PET detector, linearity, quantum efficiency (photon detection efficiency; PDE) and gain.

FIG. 2 is a graph showing a relationship between the number of micro-cells of a Geiger-mode avalanche photodiode (GAPD) of a positron emission tomography (PET) detector, linearity, quantum efficiency (photon detection efficiency; PDE) and gain.

Referring to FIG. 2, the smaller the number of the micro-cells of a GAPD photosensor, i.e. the larger the size of the micro-cells, amplification factor or quantum efficiency increases, but linearity decreases, making the GAPD photosensor inapplicable as a PET detector. On the contrary, the larger the number of the micro-cells of a GAPD photosensor, i.e. the smaller the size of the micro-cells, linearity increases, but amplification factor or quantum efficiency decreases. Thus, it is known that, because of the linearity problem, it is difficult to use a GAPD having micro-cells with a large area of 10 $\mu m^2$ or larger in the manufacture of a 3 mm×3 mm sized lutetium oxyorthosilicate (LSO)-GAPD PET detector.

Figure 3:
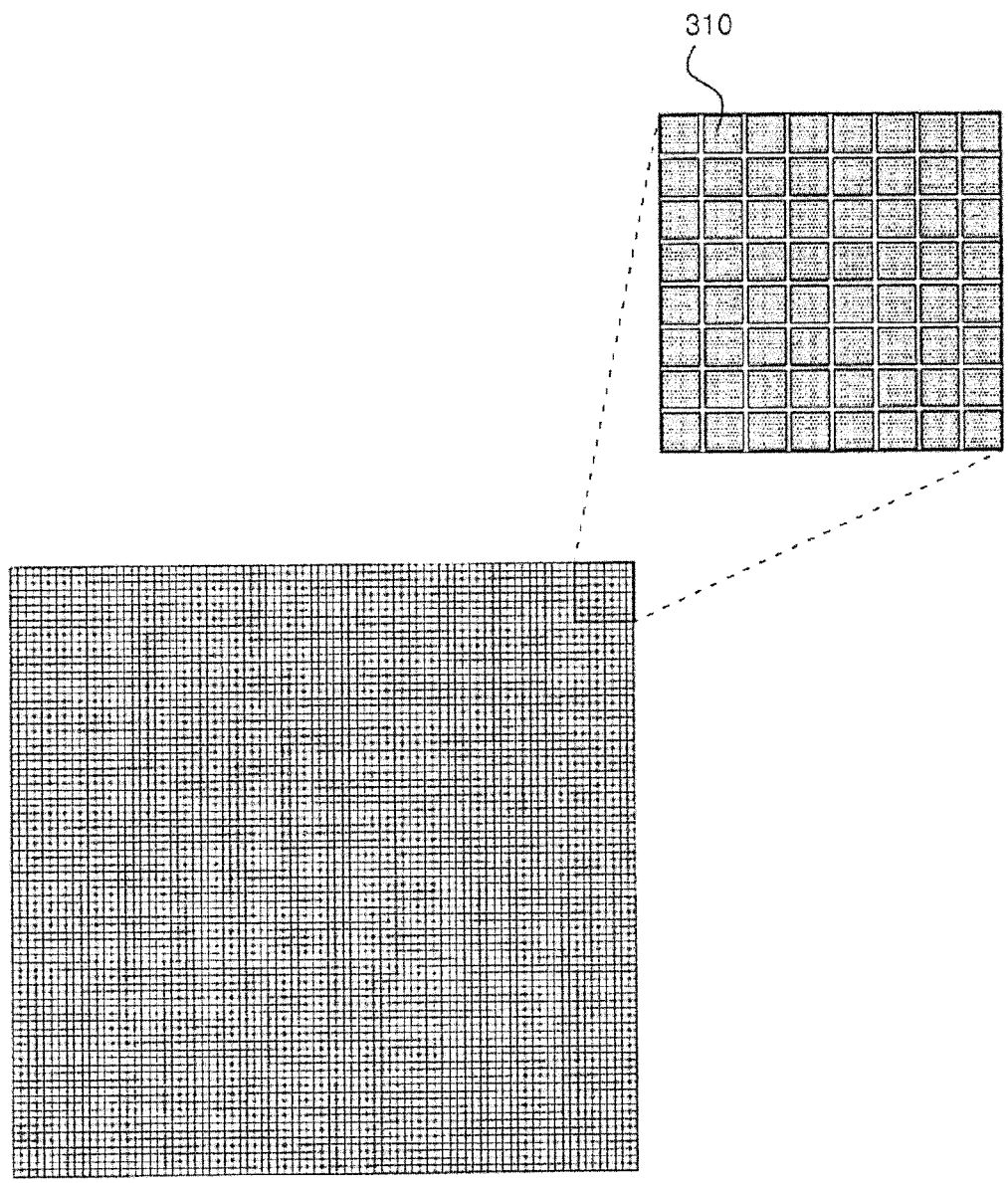
FIG. 3 shows a GAPD photosensor commonly used in a PET detector.
Figure 4:
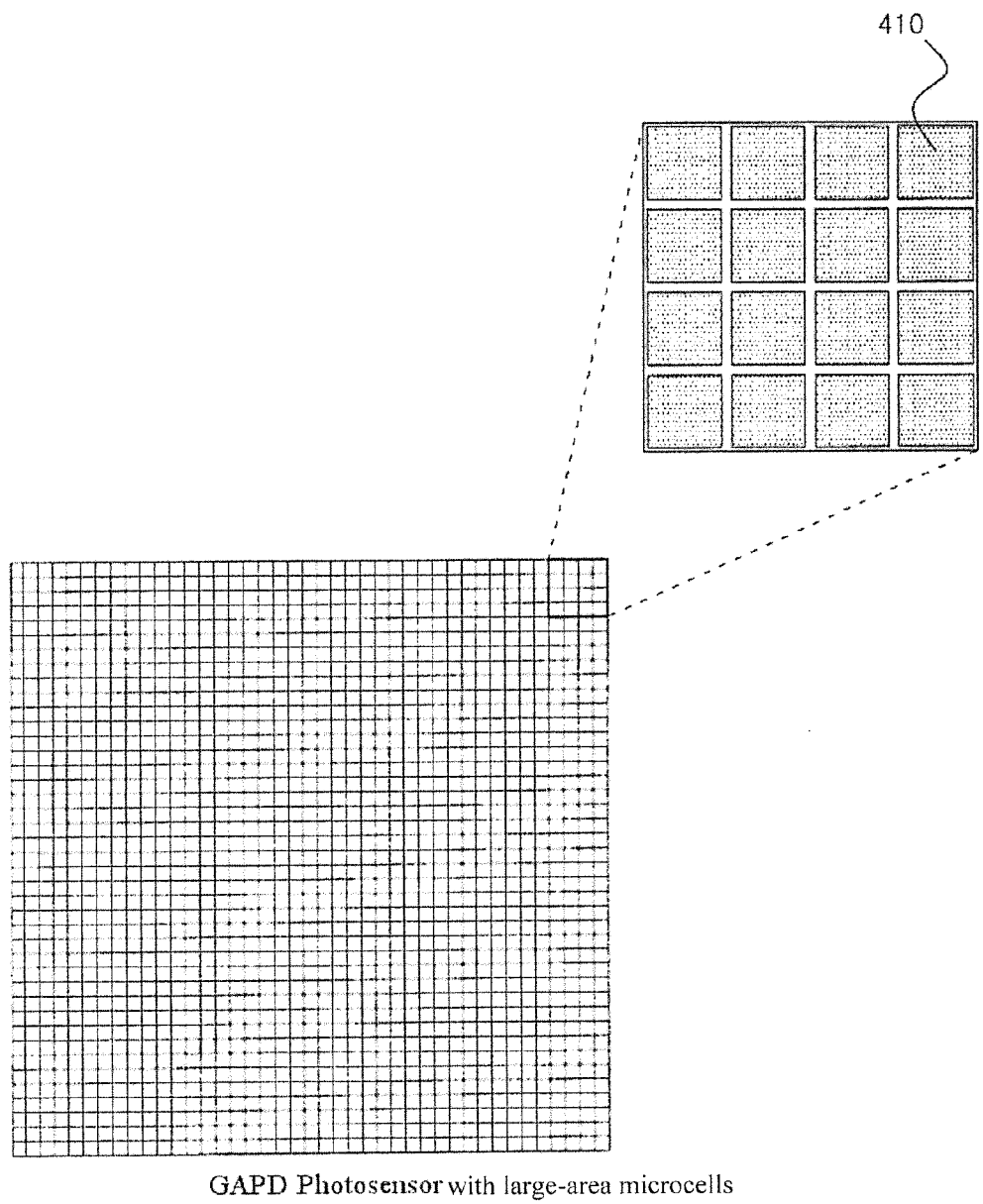
FIG. 4 shows a GAPD photosensor used in a PET detector according to an embodiment of the present disclosure.

FIG. 3 shows a GAPD photosensor commonly used in a PET detector, and FIG. 4 shows a GAPD photosensor used in a PET detector according to an embodiment of the present disclosure.

Referring to FIGS. 3 and 4, a commonly used GAPD photosensor comprises 400 micro-cells 310 having an area approximately 10 $\mu m^2$ or smaller per $mm^2$. In contrast, a GAPD photosensor according to an embodiment of the present disclosure comprises 100 to 400 micro-cells 410 having an area approximately 10 $\mu m^2$ or larger per $mm^2$. Specifically, a GAPD photosensor according to an embodiment of the present disclosure may comprise 100 micro-cells 410 having an area approximately 100 $\mu m^2$ or larger per $mm^2$.

Figure 5:
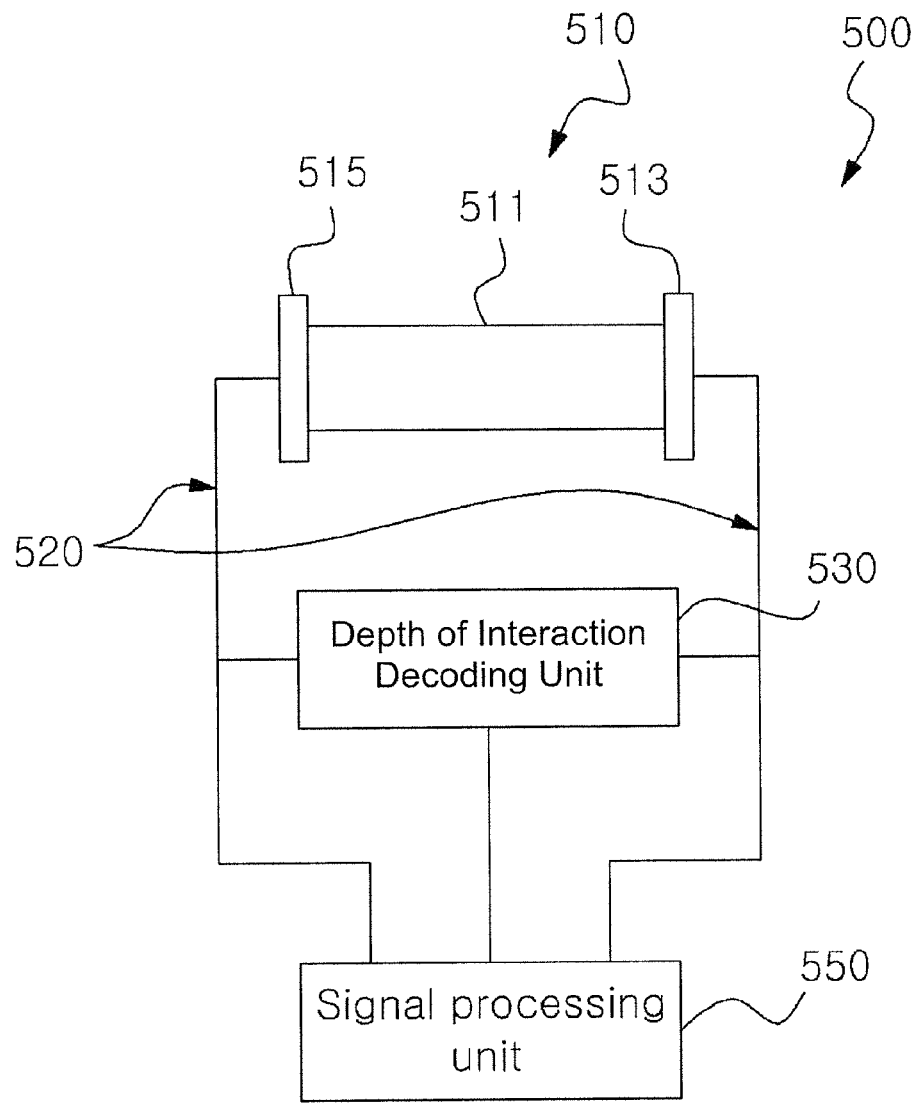
FIG. 5 shows a PET detector module according to an embodiment of the present disclosure.

FIG. 5 shows a PET detector module according to an embodiment of the present disclosure. Referring to FIG. 5, a PET detector module 500 comprises a PET detector unit 510, a cable 520, a DOI decoding unit 530 and a signal processing unit 550. A plurality of the PET detector unit 510 are arranged in various forms to constitute a PET detector. The PET detector unit 510 comprises a scintillation crystal 511, and a first GAPD photosensor 513 and a second GAPD photosensor 515 each being connected to either end of the scintillation crystal 511. The scintillation crystal 511 forms a scintillation crystal array (not shown). It detects gamma rays emitted from a living body and converting them into a scintillation light. For example, the scintillation crystal 511 detects 511 keV gamma rays emitted from a living body through a pair annihilation phenomenon toward opposite directions. The scintillation crystal may be selected from bismuth germanate (EGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr$_3$), lutetium iodide (LuI$_3$), gadolinium oxyorthosilicate (GSO), lutetium gadolinium oxyorthosilicate (LGSO) and lutetium aluminum garnet (LuAG). The signals output from the first GAPD photosensor 513 and the second GAPD photosensor 515 may be directly transferred to the DOI decoding unit 530 without the cable 520.

The first GAPD photosensor 513 and the second GAPD photosensor 515 convert the scintillation light into an electrical signal. The cable 520 transmits the electrical signal to the DOI decoding unit 530. The DOI decoding unit 530 may determine gamma ray DOI by comparing the number of the scintillation lights detected by the first GAPD photosensor 513 and the second GAPD photosensor 515. For example, it may receive the signals from the PET detector unit 510 and compare amplitude of the signals from the first GAPD photosensor 513 and the second GAPD photosensor 515, thereby determining the gamma ray DOI. As used herein, the gamma ray DOI refers to the depth where the gamma rays are incident on the scintillation crystal 511. The signal processing unit 550 provides energy and time information of the incident gamma rays from a combination of a signal output from the DOI decoding unit 530 and the signals from the PET detector unit 510.

Figure 6:
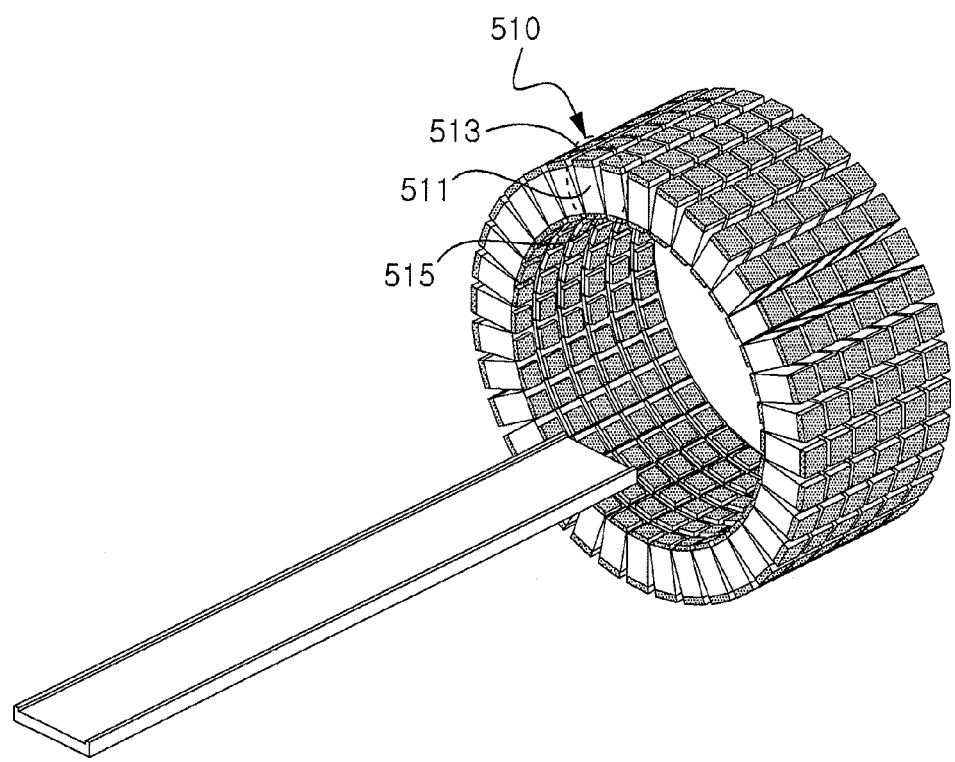
FIG. 6 shows a PET detector comprising a PET detector module according to an embodiment of the present disclosure.

FIG. 6 shows a PET detector comprising a PET detector module according to an embodiment of the present disclosure.

Referring to FIG. 6, a plurality of PET detector units 510 each comprising a scintillation crystal 511 and a first GAPD photosensor 513 and a second GAPD photosensor 515 each being connected to either end of the scintillation crystal 511 are arranged in ring shape to constitute a PET detector. Those skilled in the art will appreciate that the number of the arranged PET detector units 510 may be variously changed. The PET detector units 510 may be arranged in a matrix form, in a polygonal shape or in a ring shape so as to extend a detection area.

Figure 7:
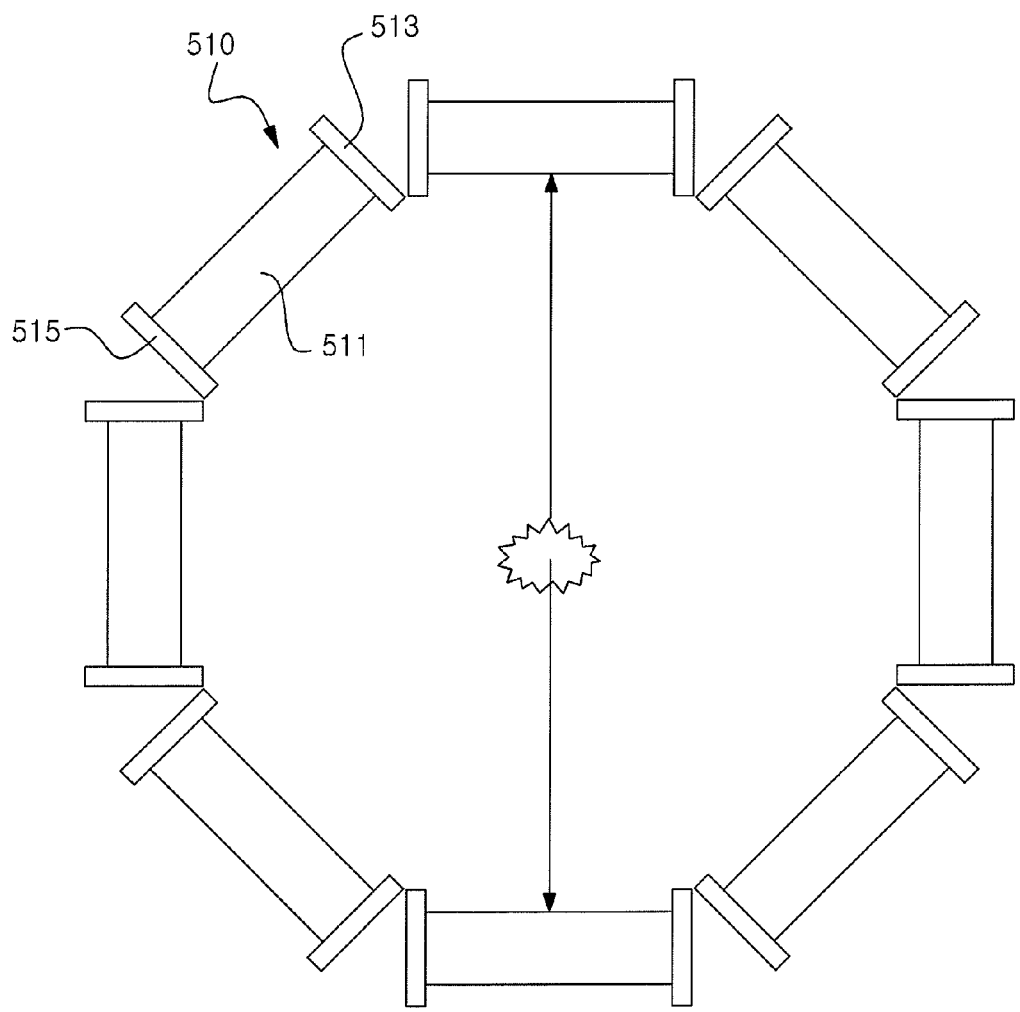
FIG. 7 shows a PET detector comprising a PET detector module according to another embodiment of the present disclosure.

FIG. 7 shows a PET detector comprising a PET detector module according to another embodiment of the present disclosure.

Referring to FIG. 7, a plurality of PET detector units 510 each comprising a scintillation crystal 511 and a first GAPD photosensor 513 and a second GAPD photosensor 515 each being connected to either end of the scintillation crystal 511 are arranged in ring shape to constitute a PET detector. The PET detector may be configured in other various shapes using the PET detector units. For example, one or more layers) of a plurality of scintillation crystals arranged in matrix form may be provided on the photosensor to constitute the PET detector.

Figure 8:
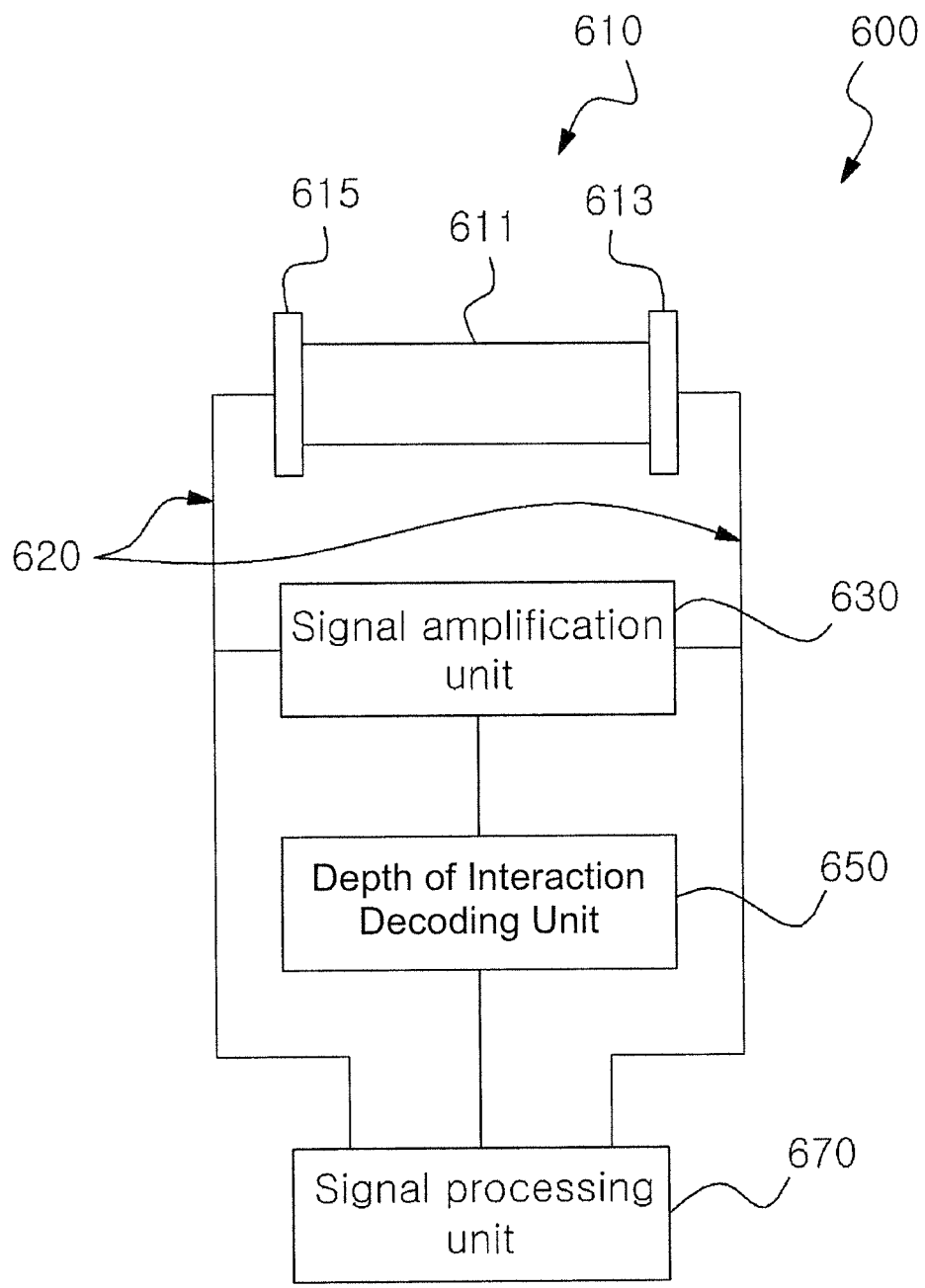
FIG. 8 shows a PET detector module according to another embodiment of the present disclosure.

FIG. 8 shows a PET detector module according to another embodiment of the present disclosure.

Referring to FIG. 8, a PET detector module 600 comprises a PET detector 610, a cable 620, a signal amplification unit 630, a DOI decoding unit 650 and a signal processing unit 670. The PET detector 610 comprises a scintillation crystal 611, and a first GAPD photosensor 613 and a second GAPD photosensor 615 each being connected to either end of the scintillation crystal 611. In the PET detector module 600, signals from the first GAPD photosensor 613 and the second GAPD photosensor 615 which convert a scintillation light into an electrical signal are transmitted to the signal amplification unit 630 via the cable 620. The signal amplification unit 630 amplifies the signals from the first GAPD photosensor 613 and the second GAPD photosensor 615 and transmits them to the DOI decoding unit 650. The DOI decoding unit 650 may determine gamma ray DOI by comparing the number of the scintillation lights detected by the first GAPD photosensor 613 and the second GAPD photosensor 615. The signal processing unit 670 provides energy and time information of the incident gamma rays from a combination of a signal output from the DOI decoding unit 650 and the signals from the PET detector unit 610.

Figure 9:
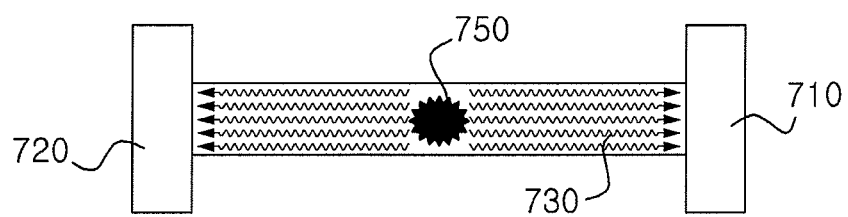
FIG. 9 illustrates an example of determining DOI using a PET detector module according to an embodiment of the present disclosure.

FIG. 9 illustrates an example of determining DOI using a PET detector module according to an embodiment of the present disclosure.

Referring to FIG. 9, a PET detector unit comprises a scintillation crystal 730 and a first GAPD photosensor 710 and a second GAPD photosensor 720 each being connected to either end of the scintillation crystal 730. As a gamma ray is incident and 10 scintillation lights are produced, 5 scintillation lights are detected by the first GAPD photosensor 710 and the remaining 5 scintillation lights are detected by the second GAPD photosensor 720. Accordingly, it is determined by the DOI decoding unit that gamma ray reaction 750 occurred at a position 0.5 in the scintillation crystal 730. For example, the gamma ray DOI may be determined by comparing amplitude of the signals detected by the first GAPD photosensor 710 and the second GAPD photosensor 720.

Figure 10:
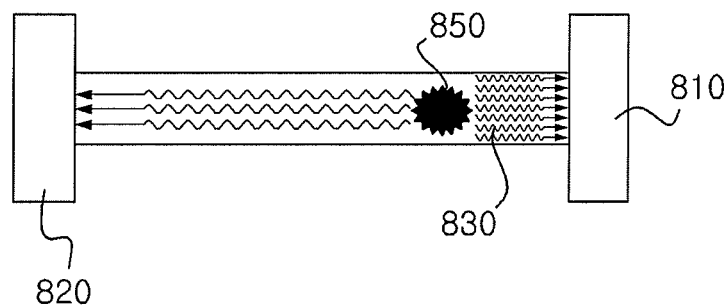
FIG. 10 illustrates an example of determining DOI using a PET detector module according to another embodiment of the present disclosure.

FIG. 10 illustrates an example of determining DOI using a PET detector module according to another embodiment of the present disclosure.

Referring to FIG. 10 a PET detector unit comprises a scintillation crystal 830 and a first GAPD photosensor 810 and a second GAPD photosensor 820 each being connected to either end of the scintillation crystal 830. As a gamma ray is incident and 10 scintillation lights are produced, 7 scintillation lights are detected by the first GAPD photosensor 810 and the remaining 3 scintillation lights are detected by the second GAPD photosensor 820. Accordingly, it is determined by the DOI decoding unit that gamma ray reaction 850 occurred at a position 0.3 in the scintillation crystal 830.

Figure 11:
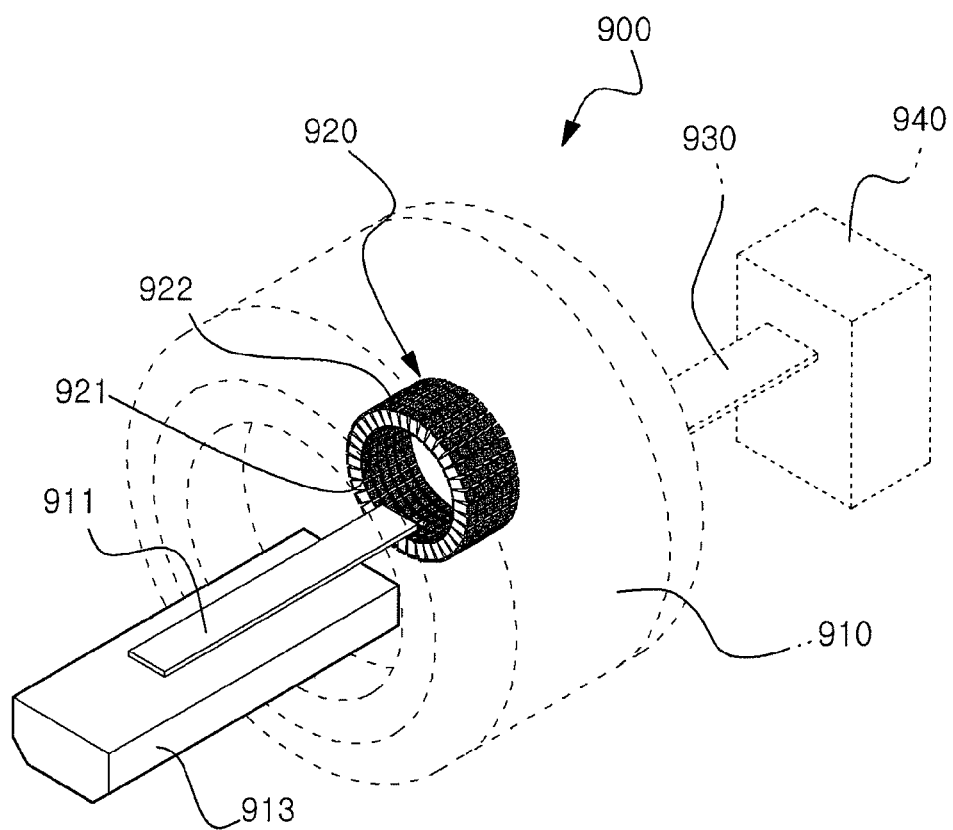
FIG. 11 shows a PET-magnetic resonance imaging (MRI) fusion system comprising a PET detector using a PET detector module according to an embodiment of the present disclosure and an MRI bore.

FIG. 11 shows a PET-magnetic resonance imaging (MRI) fusion system comprising a PET detector using a PET detector module according to an embodiment of the present disclosure and an MRI bore.

Referring to FIG. 11, a PET-MRI fusion system 900 comprises an MRI bore 910 allowing a patient to be placed therein and scanning magnetic resonance (MR) images, a PET detector 920 according to an embodiment of the present disclosure provided in the MRI bore 910, a cable 930 one end of which is connected to the PET detector 920, and a circuitry 940 connected to the other end of the cable 930.

A plurality of scintillation crystals 921 are arranged in annular shape to form a scintillation crystal array 922. The scintillation crystal array 922 is arranged in plural numbers along a length direction of the PET detector 920. On both sides of the scintillation crystals 921, a first CAPD photosensor and a second GAPD photosensor are connected, thereby configuring the PET detector 920. Each of the first GAPD photosensor and the second GAPD photosensor is connected to the circuitry 940 via the cable 930. The circuitry 940 processes the signals from the PET detector 920 and signals about the MR images from the MRI bore 910 and reconstructs the MR images and images from the PET signals.

The above PET-MRI fusion system 900 is only an example of the PET-MRI fusion system using the PET detector module according to an embodiment of the present disclosure. Those skilled in the art will appreciate that various PET-MRI fusion systems may be configured using the PET detector module according to an embodiment of the present disclosure.

Hereinafter, description will be made about the effect of the PET detector and PET detector module according to an embodiment of the present disclosure.

Suppose that a PET detector is configured according to an embodiment of the present disclosure using a 3×3 mm² sized GAPD consisting of 900 micro-cells and having a photon detection efficiency (PDE) of 50%. Assuming that a total of 6,000 photons are incident on the GAPD, the number of fired micro-cells is calculated by Equation 1:

$$N_{fired\_microcell} = N_{total\_microcells}\left[1 - e^{\left(-\varepsilon \frac{N_{photons}}{N_{total\_microcells}}\right)}\right] \quad \text{Equation 1}$$

where $N_{fired\_microcell}$ is the number of the fired micro-cells, $N_{total\_microcells}$ is the number of the total micro-cells, $N_{photons}$ is the number of the incident photons, and $\varepsilon$ is the photon detection efficiency. The photon detection efficiency $\varepsilon$ is given as Equation 2.

$$\varepsilon = Q \cdot E \times F \times \varepsilon_{Geiger} \quad \text{Equation 2}$$

where Q·E is the quantum efficiency, F is the fill factor and $\varepsilon_{Geiger}$ is the probability of Geiger mode reaction.

The total number of the fired micro-cells is 868 when a general PET detector is used, whereas it is 1460 when a PET detector according to an embodiment of the present disclosure is used. The number of the fired micro-cells is 730 for one GAPD, and the total number of the fired micro-cells is 1460 for two GAPDs.

Figure 12:
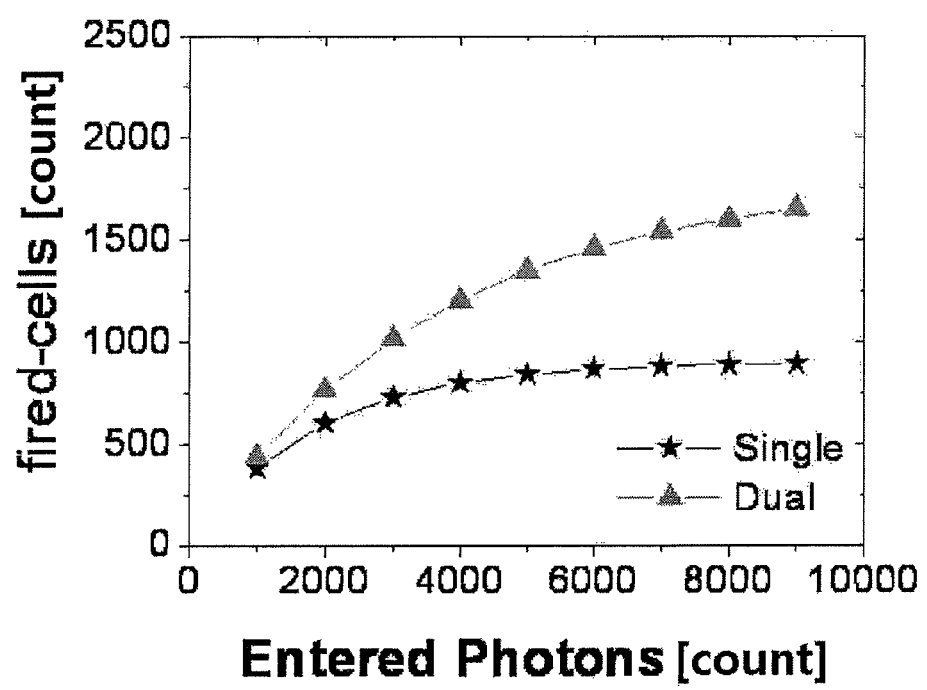
FIG. 12 is a graph showing a relationship between the number of incident photons and the number of fired microcells.

FIG. 12 is a graph showing a relationship between the number of incident photons and the number of the fired micro-cells.

Referring to FIG. 12, a (dual) PET detector according to an embodiment of the present disclosure was compared with an existing (single) PET detector for the same gamma rays with the same number of photons. More electrons were output when the (dual) PET detector according to an embodiment of the present disclosure was used. Therefore, the (dual) PET detector according to an embodiment of the present disclosure can provide more accurate information about energy and linearity.

Figure 13:
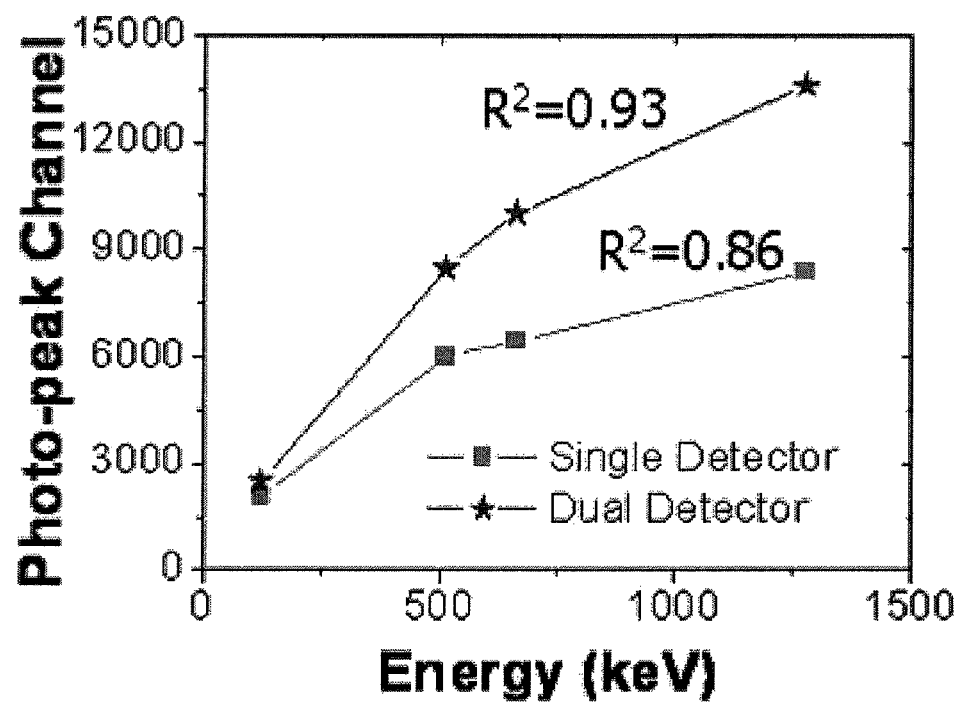
FIG. 13 is a graph showing linearity of a PET detector module according to an embodiment of the present disclosure.

FIG. 13 is a graph showing linearity of a PET detector module according to an embodiment of the present disclosure.

The linearity is an index indicating whether the number of output electrons (y-axis) is proportional to the energy of incident gamma ray (x-axis). Referring to FIG. 13, an existing photosensor comprising a single GAPD shows a linearity of 86%. In contrast, a PET detector module according to an embodiment of the present disclosure shows an improved linearity of 93%. With the PET detector module according to an embodiment of the present disclosure, the 511 keV gamma ray can be distinguished well linearly.

Figure 14:
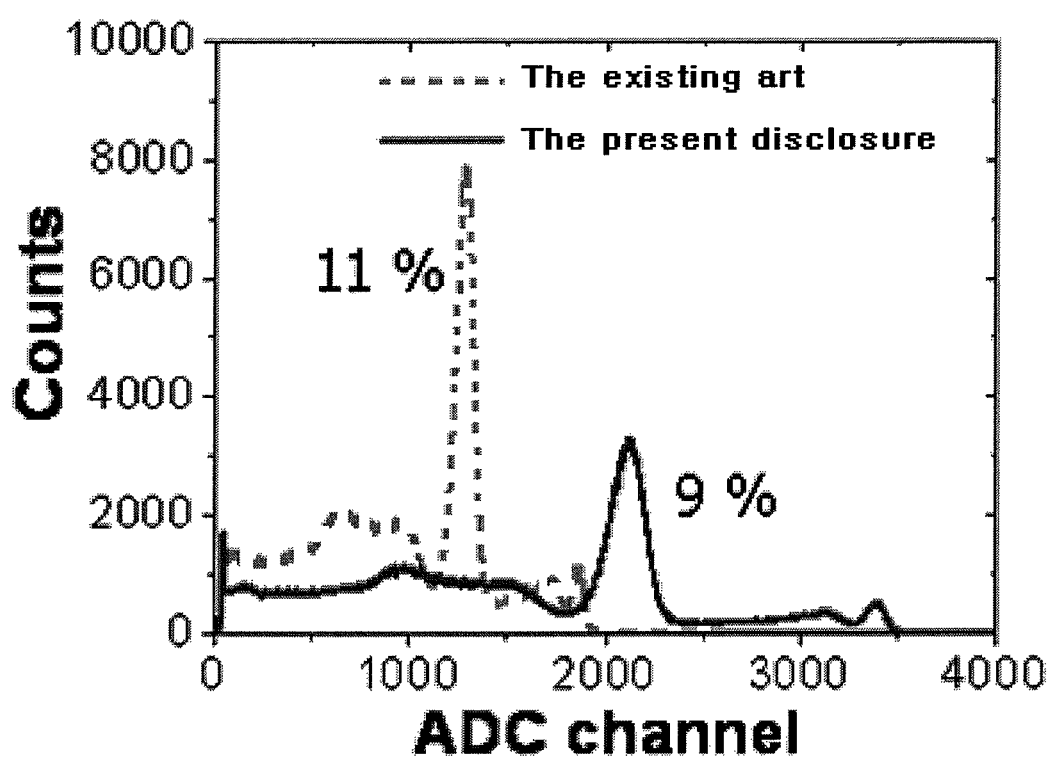
FIG. 14 is a graph showing energy resolution of a PET detector module according to an embodiment of the present disclosure.

FIG. 14 is a graph showing energy resolution of a PET detector module according to an embodiment of the present disclosure.

Referring to FIG. 14, it is shown with what error probability a PET detector can detect the 511 keV gamma ray through energy spectrum analysis. The degree of the error probability is referred to as energy resolution. An existing photosensor comprising a single GAPD shows an energy resolution of 11%. In contrast, the PET detector module according to an embodiment of the present disclosure shows an energy resolution of 9%. That is, the PET detector module according to an embodiment of the present disclosure exhibits an improved energy resolution.

The term "module" used in the specification refers to, but is not limited to, a software or hardware component, such as a field-programmable gate array (FPGA) or an application-specific integrated circuit (ASIC), which executes certain tasks. A module may be configured to reside in the addressable storage medium, and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, databases structures, tables, arrays and variables. The functionality provided for in the components and modules may be combined into fewer components and modules or further separated into additional components and modules. In addition, the components and modules may be implemented such that they execute one or more CPU(s) in a device or a secure multimedia card.

The specific numbers used in the above embodiments are given only to describe the embodiments of the present disclosure, and the present disclosure is not limited by those specific numbers.

The functionalities described above may be implemented by a processor such as a microprocessor, a controller, a microcontroller, an ASIC, etc. according to software or program codes coded to execute such functionalities. Designing, development and implementation of such codes will be easily understood by those skilled in the art based on the description of the present disclosure.

While the present disclosure has been described with respect to the specific embodiments, it will be apparent to those skilled in the art that various changes and modifications may be made without departing from the spirit and scope of the disclosure as defined in the following claims.

What is claimed is:

1. A positron emission tomography (PET) detector module comprising:
   a PET detector unit comprising a scintillation crystal configured to detect gamma rays emitted from a living body and convert them into a scintillation light and a first Geiger-mode avalanche photodiode (GAPD) photosensor and a second GAPD photosensor each being directly connected to either end of the scintillation crystal and configured to convert the scintillation light into an electrical signal; and
   a depth of interaction (DOI) decoding unit configured to receive the signals from the PET detector unit and compare amplitudes of the signals detected by the first GAPD photosensor and the second GAPD photosensor, thereby providing DOI information where the gamma rays are incident on the scintillation crystal.

2. The PET detector module according to claim 1, wherein the first GAPD photosensor and the second GAPD photosensor are a GAPD comprising micro-cells with an area of 10 $\mu m^2$ or larger.

3. The PET detector module according to claim 1, which further comprises a signal processing unit configured to provide energy and time information of the incident gamma rays from a combination of a signal output from the DOI decoding unit and the signals from the PET detector unit.

4. The PET detector module according to claim 1, wherein the scintillation crystal is selected from bismuth germanate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide ($LaBr_3$), lutetium iodide ($LuI_3$), gadolinium oxyorthosilicate (GSO), lutetium gadolinium oxyorthosilicate (LGSO) and lutetium aluminum garnet (LuAG).

5. The PET detector module according to claim 1, wherein the first GAPD photosensor and the second GAPD photosensor are a GAPD comprising micro-cells with an area of 100 $\mu m^2$.

6. A positron emission tomography (PET) detector module comprising:
   a PET detector unit comprising a scintillation crystal configured to detect 511 keV gamma rays emitted from a living body through a pair annihilation phenomenon toward opposite directions and convert them into a scintillation light and a first Geiger-mode avalanche photodiode (GAPD) photosensor and a second GAPD photosensor each being directly connected to either end of the scintillation crystal and configured to convert the scintillation light into an electrical signal;
   a signal amplification unit configured to receive the signals detected by the first GAPD photosensor and the second GAPD photosensor and amplify the signals; and
   a DOI decoding unit configured to receive the signals from the signal amplification unit and compare amplitudes of the signals detected by the first GAPD photosensor and the second GAPD photosensor, thereby providing DOI information where the gamma rays are incident on the scintillation crystal.

7. The PET detector module according to claim 6, wherein the first GAPD photosensor and the second GAPD photosensor are a GAPD comprising micro-cells with an area of 10 µm² or larger.

8. The PET detector module according to claim 6, which further comprises a signal processing unit configured to provide energy and time information of the incident gamma rays from a combination of a signal output from the DOI decoding unit and the signals from the PET detector unit.

9. The PET detector module according to claim 6, wherein the scintillation crystal is selected from bismuth germanate (BGO), lutetium oxyorthosilicate (LSO), lutetium yttrium oxyorthosilicate (LYSO), lutetium aluminum perovskite (LuAP), lutetium yttrium aluminum perovskite (LuYAP), lanthanum bromide (LaBr$_3$), lutetium iodide (LuI$_3$), gadolinium oxyorthosilicate (GSO), lutetium gadolinium oxyorthosilicate (LGSO) and lutetium aluminum garnet (LuAG).

10. A positron emission tomography (PET) detector module comprising a PET detector unit comprising at least one scintillation crystal configured to detect 511 keV gamma rays emitted in opposite directions through a pair annihilation phenomenon from a living body and convert the gamma rays into a scintillation light and a first Geiger-mode avalanche photodiode (GAPD) photosensor and a second GAPD photosensor each being directly connected to either end of the at least one scintillation crystal and configured to convert the scintillation light into an electrical signal, arranged in a matrix form, in a polygonal shape or in a ring shape so as to extend a detection area.

11. The PET detector module according to claim 10, wherein the first GAPD photosensor and the second GAPD photosensor are a GAPD comprising micro-cells with an area of 10 µm² or larger.

12. A positron emission tomography (PET) detector module comprising a PET detector unit comprising at least one scintillation crystal configured to detect 511 keV gamma rays emitted in opposite directions through a pair annihilation phenomenon from a living body and convert the gamma rays into a scintillation light and a first Geiger-mode avalanche photodiode (GAPD) photosensor and a second GAPD photosensor each being directly connected to either end of the at least one scintillation crystal and configured to convert the scintillation light into an electrical signal, connected and arranged in ring shape.

13. The PET detector module according to claim 12, wherein the first GAPD photosensor and the second GAPD photosensor are a GAPD comprising micro-cells with an area of 10 µm² or larger.

14. A positron emission tomography (PET)-magnetic resonance imaging (MRI) fusion system comprising:
   an MRI bore configured to allow a patient to be placed therein and further configured to scan magnetic resonance (MR) images;
   a PET detector provided in the MRI bore and comprising at least one scintillation crystal configured to detect gamma rays emitted from a living body and convert them into a scintillation light and a first Geiger-mode avalanche photodiode (GAPD) photosensor and a second GAPD photosensor each being directly connected to either end of the at least one scintillation crystal and configured to convert the scintillation light into an electrical signal, connected and arranged in cylindrical shape; and
   a circuit configured to process signals about the MR images from the MRI and the signals from the PET detector and reconstruct the MR images and images from the PET signals.

15. The PET detector module according to claim 14, wherein the first GAPD photosensor and the second GAPD photosensor are a GAPD comprising micro-cells with an area of 10 µm² or larger.

* * * * *